(12) United States Patent
Reinsdorf et al.

(10) Patent No.: US 12,311,342 B2
(45) Date of Patent: May 27, 2025

(54) MATERIALS COMPRISING CARBON-EMBEDDED COBALT NANOPARTICLES, PROCESSES FOR THEIR MANUFACTURE, AND USE AS HETEROGENEOUS CATALYSTS

(71) Applicant: EVONIK OPERATIONS GMBH, Essen (DE)

(72) Inventors: Arne Reinsdorf, Darmstadt (DE); Dorit Wolf, Oberursel (DE); Renat Kadyrov, Frankfurt (DE); Sarah Chamski, Freigericht (DE)

(73) Assignee: Evonik Operations GmbH, Essen (DE)

( * ) Notice: Subject to any disclaimer, the term of this patent is extended or adjusted under 35 U.S.C. 154(b) by 558 days.

(21) Appl. No.: 17/640,175

(22) PCT Filed: Sep. 3, 2020

(86) PCT No.: PCT/EP2020/074523
§ 371 (c)(1),
(2) Date: Mar. 3, 2022

(87) PCT Pub. No.: WO2021/043858
PCT Pub. Date: Mar. 11, 2021

(65) Prior Publication Data
US 2022/0314202 A1    Oct. 6, 2022

(30) Foreign Application Priority Data

Sep. 5, 2019 (EP) .................................... 19195500

(51) Int. Cl.
*B01J 21/18* (2006.01)
*B01J 23/75* (2006.01)
(Continued)

(52) U.S. Cl.
CPC ............... *B01J 21/18* (2013.01); *B01J 23/75* (2013.01); *B01J 23/8892* (2013.01); *B01J 35/23* (2024.01);
(Continued)

(58) Field of Classification Search
CPC . B01J 21/18; B01J 35/394; B01J 35/23; B01J 35/40; B01J 35/399; B01J 23/75;
(Continued)

(56) References Cited

U.S. PATENT DOCUMENTS

| 2,830,994 A | 4/1958 | Gasson et al. |
| 4,361,707 A | 11/1982 | Habib et al. |

(Continued)

FOREIGN PATENT DOCUMENTS

| CA | 2805293 A1 * | 8/2006 | ............. B01J 23/40 |
| CN | 102125844 | 7/2011 | |

(Continued)

OTHER PUBLICATIONS

International Search Report for international application PCT/EP2022/054319 filed Feb. 22, 2022, corresponding to copending U.S. Appl. No. 18/279,387.

(Continued)

*Primary Examiner* — Patricia L. Hailey
(74) *Attorney, Agent, or Firm* — Law Office of: Michael A. Sanzo, LLC

(57) ABSTRACT

The present invention relates to catalytically active material, comprising grains of non-graphitizing carbon with cobalt nanoparticles dispersed therein, wherein $d_p$, the average diameter of cobalt nanoparticles in the non-graphitizing carbon grains, is in the range of 1 nm to 20 nm, D, the average distance between cobalt nanoparticles in the non-graphitizing carbon grains, is in the range of 2 nm to 150 nm, and ω, the combined total mass fraction of metal in the (Continued)

non-graphitizing carbon grains, is in the range of 30 wt % to 70 wt % of the total mass of the non-graphitizing carbon grains, and wherein $d_p$, D and ω conform to the following relation: $4.5\ d_p/\omega \geq D \geq 0.25\ d_p/\omega$. The present invention, further, relates to a process for the manufacture of material according to the invention, as well as its use as a catalyst.

20 Claims, 1 Drawing Sheet

(51) Int. Cl.
| | |
|---|---|
| B01J 23/889 | (2006.01) |
| B01J 35/23 | (2024.01) |
| B01J 35/30 | (2024.01) |
| B01J 35/40 | (2024.01) |
| B01J 37/00 | (2006.01) |
| B01J 37/04 | (2006.01) |
| B01J 37/08 | (2006.01) |
| B01J 37/32 | (2006.01) |
| C07C 29/145 | (2006.01) |
| C07C 67/303 | (2006.01) |
| C07C 209/26 | (2006.01) |
| C07C 209/48 | (2006.01) |
| C07C 209/52 | (2006.01) |

(52) U.S. Cl.
CPC ........... *B01J 35/394* (2024.01); *B01J 35/399* (2024.01); *B01J 35/40* (2024.01); *B01J 37/0045* (2013.01); *B01J 37/04* (2013.01); *B01J 37/084* (2013.01); *B01J 37/086* (2013.01); *B01J 37/32* (2013.01); *C07C 29/145* (2013.01); *C07C 67/303* (2013.01); *C07C 209/26* (2013.01); *C07C 209/48* (2013.01); *C07C 209/52* (2013.01)

(58) Field of Classification Search
CPC .... B01J 23/8892; B01J 37/0045; B01J 37/04; B01J 37/084; B01J 37/086; B01J 37/32; C07C 29/145; C07C 67/303; C07C 209/26; C07C 209/48; C07C 209/52; C10G 2/332; C10G 2/50; C10G 2400/20; C10G 2400/22
USPC ........................................ 502/182, 185, 325
See application file for complete search history.

(56) References Cited

U.S. PATENT DOCUMENTS

| | | | |
|---|---|---|---|
| 6,417,133 B1 * | 7/2002 | Ebner | B01J 23/40 |
| | | | 502/185 |
| 9,295,979 B2 | 3/2016 | Cai et al. | |
| 10,766,847 B2 | 9/2020 | Krill et al. | |
| 11,224,859 B2 | 1/2022 | Rong et al. | |
| 12,168,220 B2 | 12/2024 | Reinsdorf et al. | |
| 2009/0087372 A1 | 4/2009 | Buchholz et al. | |
| 2010/0125035 A1 | 5/2010 | Zhang et al. | |
| 2012/0024757 A1 | 2/2012 | Xia et al. | |
| 2017/0100706 A1 | 4/2017 | Hass et al. | |
| 2017/0141405 A1 | 5/2017 | Neumann et al. | |
| 2017/0354962 A1 | 12/2017 | D'Souza et al. | |
| 2019/0143306 A1 | 5/2019 | Decottignies et al. | |
| 2020/0269215 A1 | 8/2020 | Rong et al. | |
| 2022/0298088 A1 * | 9/2022 | Tenhumberg | B01D 3/40 |
| 2022/0323941 A1 | 10/2022 | Reinsdorf et al. | |
| 2022/0347658 A1 | 11/2022 | Reinsdorf et al. | |

FOREIGN PATENT DOCUMENTS

| | | | | |
|---|---|---|---|---|
| CN | 102244253 | | 11/2011 | |
| CN | 102274726 | | 12/2011 | |
| CN | 102560530 | | 7/2012 | |
| CN | 103466606 | | 12/2013 | |
| CN | 106732733 | | 5/2017 | |
| CN | 107570160 | | 1/2018 | |
| CN | 110034306 | | 7/2019 | |
| EP | 0309221 | | 3/1989 | |
| KR | 20050001441 A | * | 1/2005 | ............ H01M 4/926 |
| WO | WO 2007/044614 | | 4/2007 | |
| WO | WO 2014/039829 | | 3/2014 | |
| WO | WO 2015/080274 | | 6/2015 | |
| WO | WO 2020/158741 | | 2/2021 | |
| WO | WO 2021/043858 | | 3/2021 | |
| WO | WO 2021/043861 | | 3/2021 | |
| WO | WO 2021/043868 | | 3/2021 | |

OTHER PUBLICATIONS

Written Opinion of the International Searching Authority for international application PCT/EP2022/054319 filed Feb. 22, 2022, corresponding to copending U.S. Appl. No. 18/279,387.
International Preliminary Report on Patentability for international application PCT/EP2022/054319 filed Feb. 22, 2022, corresponding to copending U.S. Appl. No. 18/279,387.
European Search Report and Search Opinion for EP 21159856 filed Mar. 1, 2021 corresponding to PCT/EP2022/054319.
U.S. Appl. No. 18/279,387, filed Aug. 30, 2023, Wolf.
International Search Report for corresponding PCT/EP2020/074523, filed Sep. 3, 2020.
Written Opinion of the International Searching Authority for corresponding PCT/EP2020/074523, filed Sep. 3, 2020.
International Preliminary Report on Patentability for corresponding PCT/EP2020/074523, filed Sep. 3, 2020.
European Search Report and Search Opinion for EP 19195500.4, Sep. 5, 2019, corresponding to PCT/EP2020/074523.
International Search Report for international application PCT/EP2020/074527, filed Sep. 3, 2020, corresponding to copending U.S. Appl. No. 17/640,211.
Written Opinion of the International Searching Authority for international application PCT/EP2020/074527, filed Sep. 3, 2020, corresponding to copending U.S. Appl. No. 17/640,211.
International Preliminary Report on Patentability for international application PCT/EP2020/074527, filed Sep. 3, 2020, corresponding to copending U.S. Appl. No. 17/640,211.
European Search Report and Search Opinion for EP 19195501.2 filed Sep. 5, 2019, corresponding to PCT/EP2020/074527.
International Search Report for international application PCT/EP2020/074536, filed Sep. 3, 2020, corresponding to copending U.S. Appl. No. 17/640,251.
Written Opinion of the International Searching Authority for international application PCT/EP2020/074536, filed Sep. 3, 2020, corresponding to copending U.S. Appl. No. 17/640,251.
International Preliminary Report on Patentability for international application PCT/EP2020/074536, filed Sep. 3, 2020, corresponding to copending U.S. Appl. No. 17/640,251.
European Search Report and Search Opinion for EP 19195503.8 filed Sep. 5, 2019, corresponding to PCT/EP2020/074536.
Albers, et al., "Neutron scattering study of the terminating protons in the basic structure units of non-graphitising and graphitizing carbons," *Carbon* 109:239-245 (Nov. 2016).
Banerjee, et al., "Convenient and Mild Epoxidation of Alkenes Using Heterogeneous Cobalt Oxide Catalysts," *Angew. Chem* 126:4448-4452 (Apr. 2014).
Hernández Mejía, et al., "Activity enhancement of cobalt catalysts by tuning metal-support interactions," *Nature Communication* 9:1-8 (2018).
Oschatz, et al., "Effects of calcination and activation conditions on ordered mesoporous carbon supported iron catalysts for production of lower olefins from synthesis gas," *Catal. Sci. Technol.* 6:8464-8473 (2016).
Parker, et al., "The effect of particle size, morphology and support on the formation of palladium hydride in commercial catalysts," *Chem. Sci.* 10:480-489 (2019).

(56) References Cited

OTHER PUBLICATIONS

Sietsma, et al., "Highly active cobalt-on-silica catalysts for the Fischer-Tropsch synthesis obtained via a novel calcination procedure," *Studies in Surface Science & Catalysis* 167:55-60 (2007).

Van Deelen, et al., "Assembly and activation of supported cobalt nanocrystal catalysts for the Fischer-Tropsch synthesis," *Che. Commun.* 54:2530-2533 (2018).

Van Deelen, et al., "Preparation of Cobalt Nanocrystals Supported on Metal Oxides to Study Particle Growth in Fischer-Tropsch Catalysts," *ACS Catal.* 8:10581-10589 (Oct. 2018).

Westerhaus, et al., "Heterogenized cobalt oxide catalysts for nitroarene reduction by pyrolysis of molecularly defined complexes," *Nature Chemistry* 5:537-543 (Jun. 2013).

U.S. Appl. No. 17/640,211, filed Mar. 3, 2022, Reinsdorf.
U.S. Appl. No. 17/640,251, filed Mar. 3, 2022, Reinsdorf.

\* cited by examiner

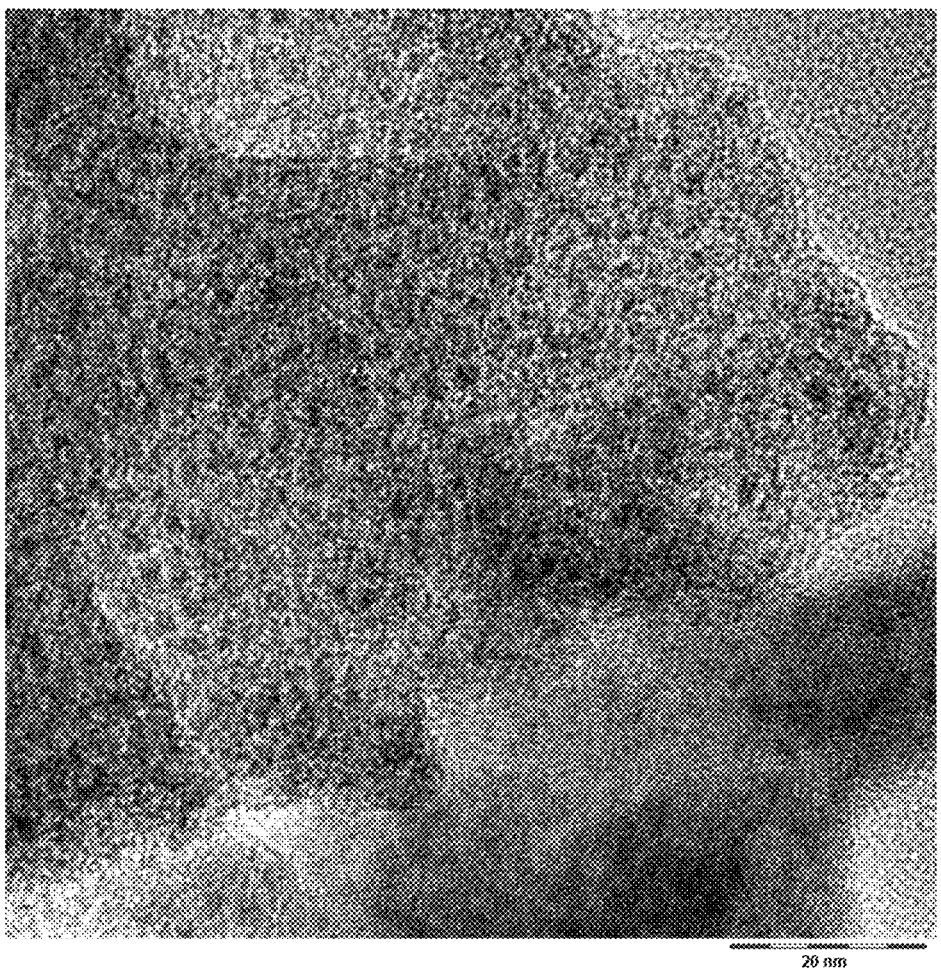

MATERIALS COMPRISING CARBON-EMBEDDED COBALT NANOPARTICLES, PROCESSES FOR THEIR MANUFACTURE, AND USE AS HETEROGENEOUS CATALYSTS

CROSS REFERENCE TO RELATED APPLICATIONS

The present application is US national stage of international application PCT/EP2020/074523, which had an international filing date of Sep. 3, 2020 and which was published on Mar. 11, 2021. The PCT application claims priority to EP 19195500.4, filed on Sep. 5, 2019. The content of these prior filings is hereby incorporated by reference in its entirety.

BACKGROUND

The present invention relates to a material, comprising grains of non-graphitizing carbon with cobalt nanoparticles dispersed therein. The material according to the invention is catalytically active in a variety of chemical reactions and can be obtained by a facile procedure.

The carbon phase of the invention is largely amorphous and does not appear to be activated carbon, carbon black, graphite, graphitized carbon black or paracrystalline carbon.

THE PRIOR ART

Significant prior art-efforts have been directed at synthesizing transition metal nanoparticles, including transition metal nanoparticles with catalytic activity in particular. As nanoparticles per se, however, cannot be employed in most heterogeneously catalyzed processes, further endeavors were conducted to develop materials containing transition metal nanoparticles attached to suitable supports, substrates or wafers. Prior art approaches for this purpose were mostly based upon impregnation or chemical vapor deposition of metal precursors onto porous or mesoporous supports (Sietsma, Jelle R. A., et al. "Highly active cobalt-on-silica catalysts for the fischer-tropsch synthesis obtained via a novel calcination procedure." Studies in Surface Science and Catalysis (2007); Van Deelen, T. W., et al. "Assembly and activation of supported cobalt nanocrystal catalysts for the Fischer-Tropsch synthesis." Chemical Communications (2018).) or using well defined ligands for the metal species and applying high temperature treatment (Westerhaus, Felix A., et al. "Heterogenized cobalt oxide catalysts for nitroarene reduction by pyrolysis of molecularly defined complexes" Nature Chemistry (2013); Banerjee, Debasis, et al. "Convenient and Mild Epoxidation of Alkenes Using Heterogeneous Oxide Catalysts" Angewandte Chemie, International Edition (2014).) Interactions of nanoparticles and support, however, were found to bring about significant limitations (Oschatz, M., et al. "Effects of calcination and activation conditions on ordered mesoporous carbon supported iron catalysts for production of lower olefins from synthesis gas" Catalysis Science & Technology (2016).) Prior art procedures, in particular, failed to yield materials exhibiting high dispersion and uniform coordination of transition metal-/metal oxide-nanoparticles in combination with high metal content. Most prior art transition metal nanoparticle materials in fact, exhibit rather low active metal concentrations of less than 20 wt % as a result of clustering and a corresponding loss of dispersion of metal particles at higher metal concentrations (Hernández Mejia, Carlos, Tom W. van Deelen and Krijn P de Jong. "Activity enhancement of cobalt catalysts by tuning metal-support interactions" Nature Communications (2018); Oschatz, M., et al. "Effects of calcination and activation conditions on ordered mesoporous carbon supported iron catalysts for production of lower olefins from synthesis gas." Catalysis Science & Technology (2016)). In view of the fact that materials exhibiting high dispersion and uniform coordination of transition metal-/metal oxide-nanoparticles in combination with high metal content are currently unavailable while such properties are considered as desirable, in order to obtain material with high catalytic activity, there is a need in the art for providing such materials as well as processes for their manufacture.

The present invention provides materials exhibiting the properties desired and a facile process for their manufacture.

THE PRESENT INVENTION

The present invention relates to catalytically active material, comprising grains of non-graphitizing carbon with cobalt nanoparticles dispersed therein,
wherein
$d_p$, the average diameter of cobalt nanoparticles in the non-graphitizing carbon grains, is in the range of 1 nm to 20 nm,
D, the average distance between cobalt nanoparticles in the non-graphitizing carbon grains, is in the range of 2 nm to 150 nm, and
$\omega$, the combined total mass fraction of metal in the non-graphitizing carbon grains, is in the range of 30 wt % to 70 wt % of the total mass of the non-graphitizing carbon grains,
wherein $d_p$ and D are measured by TGZ-TEM as described herein,
and wherein
$d_p$, D and $\omega$ conform to the following relation:

$$4.5\ d_p/\omega > D \geq 0.25\ d_p/\omega.$$

Material according to the present invention can be obtained by a process comprising the following steps:
(a) providing an aqueous solution comprising metal precursor and organic carbon source,
wherein the metal precursor comprises one or a combination of more than one organic, at least partially water soluble, salts of cobalt, and
wherein the organic carbon source is one or a combination of more than one saturated, aliphatic di-, tri-, or polycarboxylic acids,
(b) spray drying or freeze drying the aqueous solution of metal precursor and organic carbon source and, thus, obtaining intermediate product P,
(c) thermo-treating intermediate product P at a temperature in the range from 200° C. to 380° C.

As a result of research underlying the present invention it was found that grains of non-graphitizing carbon with cobalt nanoparticles dispersed therein, can be obtained from aqueous solutions of metal precursors and organic carbon sources by combining
(i) spray drying or freeze drying of the aqueous solution, with
(ii) thermal treatment at moderate temperatures of the intermediate obtained from step (i).

The final product was found to exhibit high catalytic activity in a variety of chemical reactions. In the context of the present invention, any material or substance lowering the activation energy of a chemical reaction and thus increasing its rate at a particular temperature, without being consumed by the catalyzed reaction itself, is considered as catalytically active.

Variation of process conditions and examination of the materials obtained, uncovered process conditions and material properties as claimed herein.

It was found that forming aqueous solutions of metal precursors and organic carbon sources in glass beakers and slowly drying these solutions overnight in a drying cabinet did not yield intermediate products that could be transformed into grains of non-graphitizing carbon with cobalt nanoparticles dispersed therein by thermal treatment at moderate temperatures. Specifically, it was found that if the drying process was performed too slowly, significant decomposition of polycarboxylic acids and formation of carbon dioxide started too early, leading to an early loss of oxygen functionalities of the carbon source. An early loss of oxygen functionalities, however, appears to correlate with an agglomeration of metal components and a segregation of metal precursor and carbon source, ultimately yielding an irregular distribution of large size metal clusters within the carbon matrix. Without wanting to be bound by theory, thus, it appears that sufficient availability of oxygen containing functional groups during parts of the drying procedure appears to be essential for fixing metal precursors within the carbon source in a highly dispersed and regular manner.

It was, furthermore, found that thermo-treating intermediate product P at temperatures below 200° C. and above 380° C. did not yield grains of non-graphitizing carbon according to the invention with cobalt nanoparticles dispersed therein. In particular, it was found that the proportion of the non-graphitizing carbon phase according to the invention itself decreased when the temperatures selected for thermo-treating were too high. These phases, however, are putatively related to expedient hydrogen conductivity which, in turn, is essential for efficiently catalyzing reactions involving the conversion of hydrogen. If on the other hand, temperatures selected for thermo-treating were too low or the duration of thermo-treating was too short, the level of residual oxygen in the carbon phase obtained was too high and reduction of metal precursors remained incomplete, leading to lowered catalytic activity as a result.

It should be noted, in addition, that, in view of the prior art, formation of the non-graphitizing carbon phase of the invention, as a result of the process of the present invention, may appear to be surprising. However, without wanting to be bound by theory, it is assumed that formation of non-graphitizing carbon under low temperature conditions of the process of the present invention, is facilitated by the presence of high concentrations of metal precursors in a highly dispersed manner in intermediate product P before subsequent thermo-treating.

The process of the invention yields non-graphitizing carbon material in granular form (cf. FIG. 1). Non-graphitizing carbon can be identified by a person of skill using TEM-analysis (cf. P. W. Albers, Neutron scattering study of the terminating protons in the basic structural units of non-graphitizing and graphitizing carbons, Carbon 109 (2016), 239-245, page 241, FIG. 1c).

Experimental results obtained in conjunction with the present invention indicate that catalytic activity of material obtained by the process of the invention, correlates well with its content of grains of non-graphitizing carbon exhibiting the features of the invention.

Typically, 90% of the non-graphitizing carbon grains obtained by the process of the present invention exhibit moderate size, i.e. diameters between 2 μm and 200 μm. It was presently found that, generally, more than 95% of those moderately sized non-graphitizing carbon grains, obtained by the process of the present invention, contain cobalt nanoparticles dispersed therein that conform to the relation $4.5\, d_p/\omega > D \geq 0.25\, d_p/\omega$ (with $d_p$ denoting the average diameter of cobalt nanoparticles in the non-graphitizing carbon grains, D, denoting the average distance between cobalt nanoparticles in the non-graphitizing carbon grains, and $\omega$, denoting the combined total mass fraction of metal in the non-graphitizing carbon grains). The process of the present invention, typically, yields grains wherein, only the fraction of very small and the fraction of very large grains, i.e. the particle-fractions outside of the moderate size range between 2 μm and 200 μm, contain significant portions of grains wherein cobalt nanoparticles do not conform to the relation $4.5\, d_p/\omega > D \geq 0.25\, d_p/\omega$. Accordingly, the process of the present invention, generally, yields materials with a high content of grains containing cobalt nanoparticles, wherein cobalt nanoparticles conform to the relation $4.5\, d_p/\omega > D \geq 0.25\, d_p/\omega$. However, materials with lower contents of these grains may be obtained by other processes or dilution with other materials and are thus comprised by the present invention as well.

Accordingly, in a preferred embodiment the present invention relates to catalytically active material, comprising grains of non-graphitizing carbon with cobalt nanoparticles dispersed therein, wherein cobalt nanoparticles in more than 90% of moderately sized non-graphitizing carbon grains, i.e. non-graphitizing carbon grains with a diameter between 2 μm and 200 μm conform to the relation $4.5\, dp/\omega > D \geq 0.25\, dp/\omega$, and wherein further dp, the average diameter of cobalt nanoparticles in the non-graphitizing carbon grains, is in the range of 1 nm to 20 nm, D, the average distance between cobalt nanoparticles in the non-graphitizing carbon grains, is in the range of 2 nm to 150 nm, and $\omega$, the combined total mass fraction of metal in the non-graphitizing carbon grains, is in the range of 30 wt % to 70 wt % of the total mass of the non-graphitizing carbon grains.

In another preferred embodiment, the present invention relates to catalytically active material, comprising grains of non-graphitizing carbon with cobalt nanoparticles dispersed therein, wherein cobalt nanoparticles in more than 95% of moderately sized non-graphitizing carbon grains, i.e. non-graphitizing carbon grains with a diameter between 2 μm and 200 μm conform to the relation $4.5\, dp/\omega > D \geq 0.25\, dp/\omega$, and wherein further dp, the average diameter of cobalt nanoparticles in the non-graphitizing carbon grains, is in the range of 1 nm to 20 nm, D, the average distance between cobalt nanoparticles in the non-graphitizing carbon grains, is in the range of 2 nm to 150 nm, and $\omega$, the combined total mass fraction of metal in the non-graphitizing carbon grains, is in the range of 30 wt % to 70 wt % of the total mass of the non-graphitizing carbon grains.

The cobalt nanoparticles in the non-graphitizing carbon material of the invention are mainly composed of elementary cobalt but may also contain, for example, cobalt oxide and/or dopant metal.

Computer aided analysis of TEM-pictures (TEM=transmission electron microscopy) coupled with Degussa derived TGZ method allows to determine diameters of individual cobalt nanoparticles as well as statistical measures of sets thereof (cf. Parker et al. "The effect of particle size, morphology and support on the formation of palladium hydride in commercial catalysts" Chemical Science, 2019, 10, 480).

In the context of the present invention, the average diameter of cobalt nanoparticles, $d_p$, and the average distance D is determined by the TGZ-TEM method, as described in the following:

1. Sample Preparation

In most cases, the samples to be tested are available as powders.

The powders are usually dispersed in solvents under ultrasonic application. The ultrasonic application breaks down agglomerates into aggregates and the result is an aggregate distribution rather than a mixture of aggregates and agglomerates. A micro pipette is then used to drop a drop onto a film-coated mesh lying on a piece of filter paper. The excess liquid is quickly sucked off through the filter paper so that agglomerate formation is prevented by the drying process. The suspended grains must not be too dense, as the shape and outline of the nanoparticles cannot be clearly seen through contact and overlapping of grains. An optimal dilution must be determined by test experiments with a dilution series.

In general, it can be stated that the type of preparation has hardly any effect on the result of the primary nanoparticle size evaluation.

2. Performance of the Test

The individual nanoparticles to be characterized on the basis of the TEM images must be imaged with sufficiently sharp contours.

A distribution of the nanoparticles that is not too dense with few overlaps or particles that are as separated from each other as possible on the TEM images facilitates the measurement on the TGZ3, but does not influence the measurement result.

After examining various image sections of a TEM preparation, suitable areas are selected accordingly. It should be noted that the ratio of small, medium and large nanoparticles for the respective sample is representative and characteristic and no selective preference of small or large particles is given by the operator.

The total number of primary nanoparticles to be measured depends on the scattering range of the primary nanoparticle size: the larger the scattering range, the more particles have to be measured to obtain an adequate statistical statement. For metal catalysts approx. 1500 single particles are measured. For all TGZ analysis a calibrated Hitachi H-7500 field transmission electron microscope operated at 100 keV, equipped with a CCD-Camera was used.

3. Description of the Measurement Procedure

The measurement procedure is done according to the TGZ3 manual by Carl ZEISS ("Teilchengrößenanalysator (particle size analyser) TGZ3"; Manual Fa. Carl ZEISS).

4. Measurement data processing

A detailed description of the measurement data processing is given in (F. Endter u. H. Gebauer, "Optik (Optics)" 13 (1956), 97) and (K. Seibold and M. Voll, "Distribution function for describing the particle size distribution of Soot and pyrogenic oxides". Chemiker-Zeitung, 102 (1978), Nr. 4, 131-135).

The statistical summary is compiled in the form of a report. A detailed statistical description is given in (Lothar Sachs, "Statistical methods", 5. Auflage, Springer-Verlag, Berlin (1982)).

5. Evaluation and Display of Results
   a. Total number of particles (N)
   b. Particle size distributions q0(x) and q3(x) evaluated of 1500 isolated nanoparticles per sample
   c. Particle diameter $d_n$, mean diameter ($d_n$)

$$d_n = \frac{\sum n_i d_i}{\sum n_i} = \frac{\sum n_i d_i}{n}$$

$n_i$=number of particles with diameter $d_i$
   d. Average distance D on rectangular plane $$D = \frac{1}{a^2 b^2} \int_0^b dy^* \int_0^b dy \int_0^a dx^* \int_0^a \sqrt{(x^* - x)^2 + (y^* - y)^2} \, dx$$

a, b=length, width of the rectangular plane
x, y, x*,y*=particle coordinates.

The combined total mass fraction of metal, ω, is defined as the fraction of the combined total masses of cobalt and all dopant metals, of the total mass of the material under consideration: ω=(m(cobalt)+m(dopant metals))/m(material); with m(cobalt)=total mass of cobalt in elemental form contained in the material in the form of elemental cobalt itself and/or in the form of any compounds of cobalt, m(dopant metals)=combined total mass of all dopant metals in elemental form contained in the material in the form of the elemental dopant metals themselves and/or in the form of any compounds of the dopant metals, and m(material)=total mass of material under consideration.

The combined total mass fraction of metal, ω, can be determined by means of all methods for quantitative elementary analysis, in particular XRF (X-ray fluorescence) and ICP-AES (Inductively coupled plasma atomic emission spectroscopy).

A suitable choice of conditions in the process according to the present invention allows to control the combined total mass fraction of metal, ω, in the material obtained:

Processes providing in step (a), solutions with a high metal content (cobalt and dopant metals combined), yield materials with a higher combined total mass fraction of metal, ω, than processes providing in step (a) solutions with a lower metal content.

Processes with thermo-treating in step (c) at high temperatures in the range from 200° C. to 380° C. yield materials with a higher combined total mass fraction of metal, ω, than processes with thermo-treating in step (c) at lower temperatures.

The process of the present invention yields granular material. The size of individual particles of this material as well as statistical measures of sets thereof can be determined by means of laser diffraction analysis (e.g. Cilas 1190 Series), well known to persons of skill in this field.

Typically, the process of the present invention yields granular material exhibiting the following particle size distribution: d10=5 µm, d50=40 µm, d90=150 µm.

In view of the fact that material obtained by the process according to the present invention was found to be very suitable for manufacturing shaped catalysts, in a preferred embodiment the present invention relates to catalytically active material, comprising grains of non-graphitizing carbon with cobalt nanoparticles dispersed therein, wherein $d_p$, the average diameter of cobalt nanoparticles in the non-graphitizing carbon grains, is in the range of 1 nm to 20 nm, D, the average distance between cobalt nanoparticles in the non-graphitizing carbon grains, is in the range of 2 nm to 150 nm, and ω, the combined total mass fraction of metal in the non-graphitizing carbon grains, is in the range of 30 wt % to 70 wt % of the total mass of the non-graphitizing carbon grains, and wherein $d_p$, D and ω conform to the following relation:

$$4.5\ d_p/\omega > D \geq 0.25\ d_p/\omega,$$

and wherein the non-graphitizing carbon grains exhibit the following particle size distribution: d10=5 μm, d50=40 μm, d90=150 μm.

There may be applications for materials according to the present invention, where the presence of Nitrogen is detrimental. Accordingly, in a preferred embodiment, the present invention relates to material according to the invention wherein the total mass fraction of nitrogen is less than 1 wt % of the total mass of the material.

Experimental results indicate (cf. examples 1 and 3), that material with relatively small cobalt nanoparticles may exhibit particularly attractive catalytic properties. Accordingly, in a preferred embodiment, the present invention relates to material according to the invention wherein $d_p$ is in the range of 1 nm to 10 nm. In a particularly preferred embodiment, the present invention relates to material according to the invention wherein $d_p$ is in the range of 2 nm to 6 nm.

As indicated by experimental results (cf. examples 2, 3 and 4), addition of dopant metals affects catalytic activity of the materials of the present invention. Accordingly, in a preferred embodiment, the present invention relates to material according to the invention wherein the cobalt nanoparticles have been doped with dopant metal, and wherein the dopant metal is selected from Mn, Cu or mixtures thereof, and wherein the material exhibits a molar ratio RDM=n(cobalt):n(dopant metal) in the range of 2 to 15. In a particularly preferred embodiment, the present invention relates to material according to the invention wherein the cobalt nanoparticles have been doped with dopant metal, and wherein the dopant metal is selected from Mn, Cu or mixtures thereof, and wherein the material exhibits a molar ratio RDM=n(cobalt):n(dopant metal) in the range of 4 to 10.

Experimental results indicate (cf. examples 1 and 3), that material with a very low content of Copper may exhibit particularly attractive catalytic properties. Accordingly, in a preferred embodiment, the present invention relates to material according to the invention wherein the total mass fraction of Cu is less than $10^{-4}$ wt % of the total mass of the material.

The present invention, further, relates to a process for the manufacture of the materials of the invention. As indicated above, a combination of two process steps was found to be crucial:

(i) spray drying or freeze drying of the aqueous solution of metal precursor and organic carbon source, and (ii) thermal treatment at moderate temperatures of the resulting intermediate.

Accordingly, in another aspect, the present invention is, further, directed at a process for the manufacture of material according to the invention, comprising the following steps:

(a) providing an aqueous solution comprising metal precursor and organic carbon source, wherein the metal precursor comprises one or a combination of more than one organic, at least partially water soluble, salts of cobalt, and wherein the organic carbon source is one or a combination of more than one saturated, aliphatic di-, tri-, or polycarboxylic acids, (b) spray drying or freeze drying the aqueous solution of metal precursor and organic carbon source and, thus, obtaining intermediate product P, (c) thermo-treating intermediate product P at a temperature in the range from 200° C. to 380° C.

Each of the process steps may be performed in a batch-wise or continuous format.

In another aspect the present invention is, further, directed at materials obtainable by the process of the invention.

As indicated above, formation of the materials of the present invention requires a combination of spray drying or freeze drying and suitable thermal treatment at moderate temperatures.

Accordingly, it appears reasonable to assume that only material present in solution, i.e. in dissolved form in the solution provided in step (a) of the process, can be transformed into material according to the invention. However, undissolved matter in solid form may be suspended in solution provided in step (a) as long as it does not interfere with the process forming the material of the present invention. Such solids, which may, for example, originate from undissolved metal precursor or organic carbon source, may form solid diluents of the material of the invention in the solid product obtained after step (c) of the process of the invention. Similarly, organic solvents may be dissolved or emulsified in the solution provided in step (a) as long as their presence does not interfere with the process forming the material of the present invention. However, in order to avoid interference with the process forming the material of the present invention, in preferred embodiments, the process of the invention is performed with aqueous solutions, provided in step (a), that are free of undissolved matter in solid form as well as free of organic solvents.

If no dopant metal is used, the metal precursor in the solution provided in step (a) of the process of the present invention, is one or a combination of more than one organic, at least partially water soluble, salts of cobalt. In the present context a salt is considered as being at least partially water soluble, if at least a fraction of the salt dissolves in the aqueous solution provided in step (a) under the conditions employed in the process. Preferably, if no dopant metal is used, the metal precursor in the solution provided in step (a) of the process of the present invention, is one or a combination of more than one, organic salts of cobalt, whereof the amounts desired to be included into the solution are completely soluble in the aqueous solution of step (a).

If dopant metal is used, the metal precursor in the solution provided in step (a) of the process of the present invention is a combination of one or more organic, at least partially water soluble, salts of cobalt, with one or more organic, at least partially water soluble, salts of manganese and/or copper. Preferably, if dopant metal is used, the metal precursor in the solution provided in step (a) of the process of the present invention, is a combination of one or more organic salts of cobalt with one or more organic salts of manganese and/or copper, whereof the amounts desired to be included into the solution are completely soluble in the aqueous solution of step (a).

Preferred organic anions of the metal precursors in the solution provided in step (a) of the process of the present invention are acetate, carbonate, oxalate, citrate, malonate, tartrate and glutarate. If nitrogen does not need to be avoided, nitrate is another preferred anion of the metal precursors in the solution provided in step (a).

Saturated, aliphatic di-, tri-, or polycarboxylic acids, alone or as part of a mixture, may be used as organic carbon sources of the aqueous solution provided in step (a), as long as they support formation of the materials of the present invention. In preferred embodiments, malonic acid, glutaric acid, citric acid or mixtures thereof are used as organic carbon source of the aqueous solution provided in step (a) of the process of the present invention. In a particularly preferred embodiment of the present invention, citric acid is used as organic carbon source of the aqueous solution provided in step (a) of the process of the present invention.

The aqueous solution provided in step (a) is spray dried or freeze dried in step (b) of the process of the present invention. The product obtained therefrom is referred to as intermediate product P in the context of the present invention. Process parameters for spray drying and freeze drying can be varied over a wide range as long as the drying process is performed without interruption and the combined content of water and organic solvents exhibited by intermediate product P, is below 10 wt %. In a preferred embodiment of the present invention the aqueous solution provided in step (a) is spray dried in step (b) of the process of the present invention.

Thermo-treating according to step (c) of the process of the present invention is performed under defined temperature conditions and inert gas atmosphere, e.g. nitrogen, or air. A wide range of suitable furnaces for this purpose is available commercially. In preferred embodiments, thermo-treating is performed under inert gas atmosphere, e.g. nitrogen. Heating rates during thermo-treating should be small enough to allow homogeneous distribution of heat, i.e. typically smaller than 15 K/min, preferably smaller than 10 K/min, and particularly preferred smaller than 5 K/min. Thermo treating intermediate product P is performed at a temperature in the range from 200° C. to 380° C. In preferred embodiments of the present invention, thermo treating intermediate product P is performed at a temperature in the range from 255° C. to 375° C. In particularly preferred embodiments, thermo-treating intermediate product P is performed at a temperature in the range from 300° C. to 350° C. Typically, thermo treating intermediate product P is performed for a duration of 1 to 4 hours, but thermo-treating for longer or shorter intervals of time may work as well. Heating and cooling intervals are not accounted for when determining the duration of thermo treating. In preferred embodiments thermo-treating intermediate product P is performed for a duration of 1 to 4 hours.

As indicated above, materials according to the present invention exhibit catalytic activity. Accordingly, in another aspect, the present invention, further, relates to the use of materials of the present invention as catalysts.

Materials according to the present invention can be used, for example, as catalysts in liquid phase hydrogenations of organic compounds, specifically unsaturated compounds like alkenes and alkynes, aldehydes and ketones, esters and imines, nitro compounds and nitriles. Materials according to the present invention are, further, very active catalysts for the reductive amination of carbonyl compounds. Accordingly, in another aspect, the present invention, further, relates to the use of materials of the invention as catalysts for the hydrogenation of organic compounds, the reductive amination of carbonyl compounds and/or the hydroformylation of organic compounds.

Materials according to the present invention can also be used as catalysts in the conversion of carbon monoxide, carbon dioxide or mixtures thereof, with hydrogen, to alcohols, alkenes, alkanes or mixtures thereof. Accordingly, in another aspect, the present invention, further, relates to the use of materials of the invention as catalysts for the conversion of carbon monoxide, carbon dioxide or mixtures thereof with hydrogen, to alcohols, alkenes, alkanes or mixtures thereof.

Materials according to the present invention may be used as catalysts in unmodified form or may be transformed into catalyst bodies by shaping processes (e.g. tableting, pelletizing, extrusion, coating, 3D-printing), well known to persons of skill in the art.

FIGURE LEGENDS

FIG. 1:
TEM Image of carbon embedded cobalt nanoparticles (Cat. 1b) according to the invention.

EXAMPLES

Examples 1 a,b

Preparation of Carbon Embedded Co-Nanoparticles

Carbon embedded Co-nanoparticles were prepared by dissolving 14.4 g citric acid (puriss, Sigma Aldrich) in 75 mL of deionized water under constant stirring at room temperature. In a second beaker 18.7 g Cobalt(II)-acetate tetrahydrate (($CH_3COO)_2Co*4\ H_2O$, Sigma Aldrich) was dissolved in 75 mL of deionized water under constant stirring at room temperature. The Cobalt-acetate solution was slowly added to the citric acid solution and stirred for another 30 min at room temperature. The resultant solution was spray dried using a conventional mini spray dryer (Büchi, Mini Spray Dryer B-290) with constant inlet temperature of 220° C., outlet temperature of 120° C. and 20% pump speed. The obtained powder was split into two fractions with identical mass for the final thermo-treatment.

The first sample was thermo-treated in a tubular furnace under nitrogen atmosphere, with a 180 min ramp to 300° C., where temperature was maintained for another 4 h followed by natural cooling down. The resultant catalyst powder was labeled Cat. 1a.

The second sample was thermo-treated in a similar fashion under nitrogen atmosphere. The sample was heated up to 350° C. within 180 min where temperature was maintained for 4 h followed by natural cool down. The resultant catalyst powder was labeled Cat. 1 b.

The materials exhibit the following characteristics which were determined by XRF (X-ray fluorescence) and TGZ analysis using a calibrated Hitachi H-7500 field transmission electron microscope operated at 100 keV, equipped with a CCD-Camera:

| ID | $d_P$ | ω | D |
|---|---|---|---|
| 1a | 3.0 nm | 0.54 | 7 nm |
| 1b | 3.5 nm | 0.59 | 6 nm |

Example 2

Preparation of Carbon Embedded Co—Cu-Nanoparticles

Carbon embedded Co—Cu-nanoparticles were prepared by dissolving 19.4 g citric acid (puriss, Sigma Aldrich) in 100 mL of deionized water under constant stirring at room temperature. In a second beaker 19.9 g Cobalt(II)-acetate tetrahydrate (($CH_3COO)_2Co*4\ H_2O$, Sigma Aldrich) and 3.9 g Cu(II)-acetate-Monohydrate (($CH_3COO)_2Cu*H_2O$, Alfa Aesar) were dissolved in 100 mL of deionized water under constant stirring at room temperature. The Cobalt-Copper-solution was slowly added to the citric acid solution and stirred for another 30 min at room temperature. The resultant solution was spray dried using a conventional mini spray dryer (Büchi, Mini Spray Dryer B-290) with constant inlet temperature of 220° C., outlet temperature of 130° C. and 30% pump speed. The obtained powder was thermo-treated in a tubular furnace under nitrogen atmosphere, with a 180 min ramp to 350° C., where temperature was maintained for another 4 h followed by natural cooling down. The resultant catalyst powder was labeled Cat. 2.

The materials exhibit the following characteristics which were determined by XRF (X-ray fluorescence) and TGZ analysis using a calibrated Hitachi H-7500 field transmission electron microscope operated at 100 keV, equipped with a CCD-Camera:

| ID | $d_p$ | $\omega$ | D |
|---|---|---|---|
| 2 | 5.0 nm | 0.65 | 9 nm |

Examples 3 a,b

Preparation of Carbon Embedded Co—Mn-Nanoparticles

Carbon embedded Co—Mn-nanoparticles were prepared by dissolving 14.4 g citric acid (puriss, Sigma Aldrich) in 75 mL of deionized water under constant stirring at room temperature. In a second beaker 18.7 g Cobalt(II)-acetate tetrahydrate (($CH_3COO)_2Co*4\ H_2O$, Sigma Aldrich) and 1.5 g Mn(II)-acetate tetrahydrate ($Mn(CH_3COO)_2*4\ H_2O$, Sigma Aldrich) were dissolved in 75 mL of deionized water under constant stirring at room temperature. The Cobalt-Manganese-solution was slowly added to the citric acid solution and stirred for another 30 min at room temperature. The resultant solution was spray dried using a conventional mini spray dryer (Büchi, Mini Spray Dryer B-290) with constant inlet temperature of 220° C., outlet temperature of 125° C. and 25% pump speed. The resultant powder was split into two fractions with identical mass for the final thermo-treatment.

The first sample was thermo-treated in a muffle furnace under nitrogen atmosphere, with a 180 min ramp to 300° C., where temperature was maintained for another 4 h followed by natural cooling down. The resultant catalyst powder was labeled Cat. 3a.

The second sample was thermo-treated in a similar fashion under nitrogen atmosphere. The sample was heated up to 350° C. within 180 min where temperature was maintained for 4 h followed by natural cool down. The resultant catalyst powder was labeled Cat. 3b.

The materials exhibit the following characteristics which were determined by XRF (X-ray fluorescence) and TGZ analysis using a calibrated Hitachi H-7500 field transmission electron microscope operated at 100 keV, equipped with a CCD-Camera:

| ID | $d_p$ | $\omega$ | D |
|---|---|---|---|
| 3a | 4.0 nm | 0.54 | 10 nm |
| 3b | 4.0 nm | 0.6 | 9 nm |

Examples 4 a,b

Preparation of Carbon Embedded Co—Cu—Mn-Nanoparticles

Carbon embedded Co—Cu—Mn-nanoparticles were prepared by dissolving 14.4 g citric acid (puriss, Sigma Aldrich) in 75 mL of deionized water under constant stirring at room temperature. In a second beaker 14.9 g Cobalt(II)-acetate tetrahydrate (($CH_3COO)_2Co*4\ H_2O$, Sigma Aldrich), 2.9 g Cu(II)-acetate-Monohydrate (($CH_3COO)_2Cu*H_2O$, Alfa Aesar) and 1.5 g Mn(II)-acetate tetrahydrate ($Mn(CH_3COO)_2*4\ H_2O$, Sigma Aldrich) were dissolved in 75 mL of deionized water under constant stirring at room temperature. The Cobalt-Copper-Manganese-solution was slowly added to the citric acid solution and stirred for another 30 min at room temperature. The resultant solution was spray dried using a conventional mini spray dryer (Büchi, Mini Spray Dryer B-290) with constant inlet temperature of 220° C., outlet temperature of 125° C. and 25% pump speed. The obtained powder was split into two fractions with identical mass for the final thermo-treatment.

The first sample was thermo-treated in a muffle furnace under nitrogen atmosphere, with a 180 min ramp to 300° C., where temperature was maintained for another 4 h followed by natural cooling down. The resultant catalyst powder was labeled Cat. 4a.

The second sample was thermo-treated in a similar fashion under nitrogen atmosphere. The sample was heated up to 350° C. within 180 min where temperature was maintained for 4 h followed by natural cooling down. The resultant catalyst powder was labeled Cat. 4b.

The materials exhibit the following characteristics which were determined by XRF (X-ray fluorescence) and TGZ analysis using a calibrated Hitachi H-7500 field transmission electron microscope operated at 100 keV, equipped with a CCD-Camera:

| ID | $d_p$ | $\omega$ | D |
|---|---|---|---|
| 4a | 4.5 nm | 0.51 | 11 nm |
| 4b | 5.0 nm | 0.58 | 10 nm |

Comparative Examples

For comparison to the state of the art, two "Cobalt on carbon support"-catalysts was prepared according to Westerhaus, Felix A., et al. "Heterogenized cobalt oxide catalysts for nitroarene reduction by pyrolysis of molecularly defined complexes" Nature Chemistry (2013).

A catalyst with 3 wt % Cobalt on a conventional Vulcan XC72R Carbon support was obtained according to Westerhaus et al. (Westerhaus, Felix A., et al. "Heterogenized cobalt oxide catalysts for nitroarene reduction by pyrolysis of molecularly defined complexes" Nature Chemistry (2013) page 538, table 1, entry 1) and labeled as Cat. 5.

A highly loaded catalyst with 20 wt % Cobalt on a conventional Vulcan XC72R Carbon support was obtained according to Westerhaus et al. (Westerhaus, Felix A., et al. "Heterogenized cobalt oxide catalysts for nitroarene reduction by pyrolysis of molecularly defined complexes" Nature Chemistry (2013) page 538, table 1, entry 1; with higher Co-loading) and labeled as Cat. 6.

Furthermore, a highly disperse Co/$TiO_2$ was prepared according to Van Deelen, T. W., et al. "Preparation of Cobalt Nanocrystals Supported on Metal Oxides to Study Particle Growth in Fischer—Tropsch Catalysts." ACS Catalysis (2018).

A catalyst with 7 wt % Cobalt on a conventional Evonik Aeroxide P25 $TiO_2$-support was obtained according to Van Deelen et al. (Van Deelen, T. W., et al. "Preparation of Cobalt Nanocrystals Supported on Metal Oxides to Study Particle Growth in Fischer—Tropsch Catalysts." ACS Catalysis (2018) page 10582, Incipient Wetness Impregnation) and labeled as Cat. 7.

The materials exhibit the following characteristics which were determined by XRF (X-ray fluorescence) and TGZ analysis using a calibrated Hitachi H-7500 field transmission electron microscope operated at 100 keV, equipped with a CCD-Camera:

| ID | $d_p$ | ω | D |
|---|---|---|---|
| Cat. 5 | 30 nm | 0.03 | n.d.* |
| Cat. 6 | 55 nm | 0.20 | n.d.* |
| Cat. 7 | 45 nm | 0.07 | n.d.* |

*Catalyst materials Cat. 5, Cat. 6, and Cat. 7 exhibit a very inhomogeneous distribution of their metal content, with lager metal clusters in apparently random arrangement, instead of a finely dispersed nano-particle collocation as found in the materials obtained from examples 1 to 4. Determining D-values, therefore, does not appear meaningful.

Testing Catalytic Activity

Experiments to determine Catalytic activity and selectivity of the materials were performed in a batch-wise fashion using 200 mg of catalyst and 5 mmol of substrate in 5 ml of methanol.

Autoclaves were heated to the desired reaction temperature and agitated under a constant hydrogen pressure of 50 bar for all experiments. Reaction products were filtered and analyzed by means of GC-MS.

I. Hydrogenation of Methyl Crotonate to Methyl Butyrate

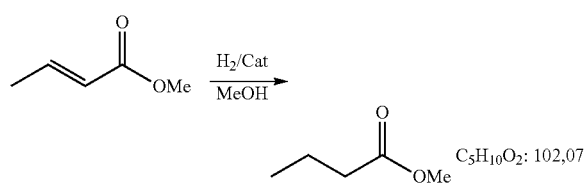

| ID | Cat. ID | Duration h | Temp. T °C. | reactant % | product % |
|---|---|---|---|---|---|
| 1 | Cat. 1 a | 3.00 | 80.00 | 0.00 | 100.00 |
| 2 | Cat. 1 b | 2.00 | 80.00 | 0.00 | 100.00 |
| 3 | Cat. 2 | 0.3 | 80.00 | 0.00 | 100.00 |
| 4 | Cat. 4 a | 2.00 | 80.00 | 0.00 | 100.00 |
| 5 | Cat. 4 b | 1.80 | 80.00 | 0.00 | 100.00 |
| 6 | Cat. 4 a | 35.00 | 25.00 | 0.00 | 100.00 |
| 7 | Cat. 4 b | 10.00 | 25.00 | 0.00 | 100.00 |
| 8 | Cat. 3 a | 8.00 | 80.00 | 0.00 | 100.00 |
| 9 | Cat. 3 b | 7.00 | 80.00 | 0.00 | 100.00 |
| 10 | Cat. 5 | 20.00 | 80.00 | 67.10 | 32.90 |
| 11 | Cat. 6 | 20.00 | 80.00 | 0.00 | 100.00 |
| 12 | Cat. 7 | 20.00 | 80.00 | 0.00 | 100.00 |

II. Hydrogenation of Acetylnaphthalene

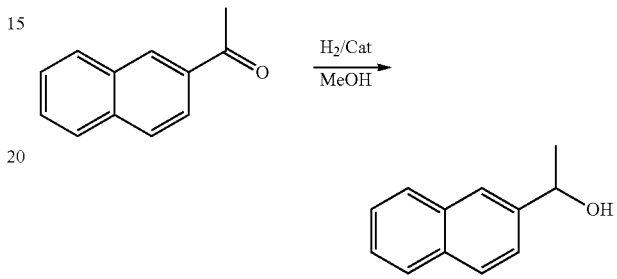

| ID | Cat. ID | Duration h | Temp. T °C. | reactant % | product % | side-product % |
|---|---|---|---|---|---|---|
| 13 | Cat. 1 a | 19.00 | 80.00 | 49.70 | 50.30 | 0.00 |
| 14 | Cat. 1 b | 19.00 | 80.00 | 0.00 | 100.00 | 0.00 |
| 15 | Cat. 2 | 19.00 | 80.00 | 0.00 | 100.00 | 0.00 |
| 16 | Cat. 4 a | 0.40 | 80.00 | 0.00 | 96.20 | 3.8 |
| 17 | Cat. 4 b | 0.25 | 80.00 | 0.00 | 95.40 | 4.6 |
| 18 | Cat. 3 a | 8.00 | 80.00 | 0.00 | 76.5 | 23.5 |
| 19 | Cat. 3 b | 8.00 | 80.00 | 41.8 | 58.2 | 0.00 |
| 20 | Cat. 5 | 20.00 | 80.00 | 98.1 | 0.00 | 1.8 |
| 21 | Cat. 6 | 20.00 | 80.00 | 49.3 | 46.7 | 4.0 |
| 22 | Cat. 7 | 20.00 | 80.00 | 97.1 | 0.00 | 2.9 |

III. Hydrogenation of N-Benzylidene-Benzylamine

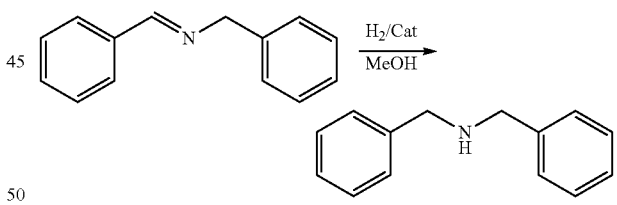

| ID | Cat. ID | Duration h | Temp T °C. | reactant % | product % | side-product % |
|---|---|---|---|---|---|---|
| 23 | Cat. 1 a | 8.00 | 100.00 | 0.00 | 89.1 | 7.10 |
| 24 | Cat. 1 b | 10.00 | 100.00 | 0.00 | 90.3 | 4.40 |
| 25 | Cat. 2 | 1.00 | 100.00 | 1.50 | 91.4 | 2.50 |
| 26 | Cat. 4 a | 6.00 | 100.00 | 0.00 | 99.2 | 0.6 |
| 27 | Cat. 4 b | 5.00 | 100.00 | 0.00 | 99.4 | 0.8 |
| 28 | Cat. 4 a | 48.00 | 25.00 | 0.00 | 100.00 | |
| 29 | Cat. 4 b | 48.00 | 25.00 | 0.00 | 100.00 | |
| 30 | Cat. 3 a | 8.00 | 100.00 | 0.00 | 98.5 | 1.5 |
| 31 | Cat. 3 b | 8.00 | 100.00 | 0.00 | 99.3 | 0.7 |
| 32 | Cat. 5 | 12.50 | 100.00 | 3.00 | 95.3 | 1.70 |
| 33 | Cat. 6 | 9.50 | 100.00 | 3.30 | 94.1 | 2.60 |
| 34 | Cat. 7 | 9.50 | 100.00 | 97.40 | 0.00 | 2.60 |

IV. Hydrogenation of Dodecannitrile

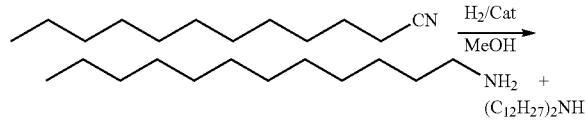

| ID | Cat. ID | Duration h | Temp. T °C. | reactant % | product % | side-product % |
|----|---------|------------|-------------|------------|-----------|----------------|
| 35 | Cat. 1 a | 18.00 | 80.00 | 81.0 | 17.50 | 1.30 |
| 36 | Cat. 1 b | 10.00 | 80.00 | 0.00 | 90.40 | 9.60 |
| 37 | Cat. 2 | 10.00 | 80.00 | 0.00 | 89.40 | 10.60 |
| 38 | Cat. 4 a | 3.00 | 80.00 | 0.00 | 100.00 | |
| 39 | Cat. 4 b | 4.00 | 80.00 | 0.00 | 75.8 | 24.2 |
| 40 | Cat. 3 a | 3.00 | 80.00 | 0.00 | 76.2 | 23.8 |
| 41 | Cat. 3 b | 4.00 | 80.00 | 53.1 | 40.4 | 6.4 |
| 42 | Cat. 5 | 20.00 | 80.00 | 100.0 | 0.00 | 0.00 |
| 43 | Cat. 6 | 20.00 | 80.00 | 29.1 | 60.7 | 10.4 |
| 44 | Cat. 7 | 20.00 | 80.00 | 95.2 | 3.3 | 1.4 |

V. Amination of Cyclohexanone

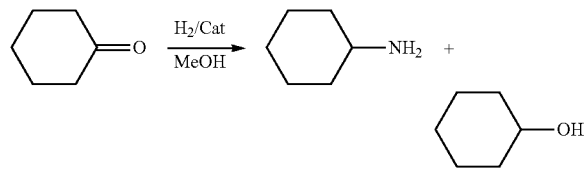

| ID | Cat. ID | Duration h | Temp T °C. | reactant % | product % | side-product % |
|----|---------|------------|------------|------------|-----------|----------------|
| 45 | Cat. 1 a | 2.00 | 100.00 | 0.00 | 89.60 | 5.80 |
| 46 | Cat. 1 b | 3.00 | 100.00 | 0.00 | 93.40 | 6.60 |
| 47 | Cat. 2 | 1.00 | 100.00 | 0.00 | 92.30 | 7.70 |
| 48 | Cat. 4 a | 2.00 | 100.00 | 0.00 | 64.6 | 35.4 |
| 49 | Cat. 4 b | 2.00 | 100.00 | 0.00 | 81.7 | 18.3 |
| 50 | Cat. 3 a | 2.00 | 100.00 | 0.00 | 90.0 | 10.0 |
| 51 | Cat. 3 b | 2.00 | 100.00 | 0.00 | 89.9 | 10.1 |
| 52 | Cat. 5 | 24.0 | 100.00 | 24.4 | 9.2 | 66.5 |
| 53 | Cat. 6 | 24.0 | 100.00 | 0.00 | 85.7 | 14.3 |
| 54 | Cat. 7 | 24.0 | 100.00 | 0.00 | 72.1 | 27.9 |

The invention claimed is:

1. Catalytically active material, comprising grains of non-graphitizing carbon with cobalt nanoparticles dispersed therein, wherein:
   $d_p$, the average diameter of cobalt nanoparticles in the non-graphitizing carbon grains, is in the range of 1 nm to 20 nm;
   D, the average distance between cobalt nanoparticles in the non-graphitizing carbon grains, is in the range of 2 nm to 150 nm; and
   $\omega$, the combined total mass fraction of metal in the non-graphitizing carbon grains, is in the range of 30 wt % to 70 wt % of the total mass of the non-graphitizing carbon grains;
   wherein $d_p$ and D are measured by TGZ-TEM, and $d_p$, D and $\omega$ conform to the following relation: $4.5\, d_p/\omega \geq D \geq 0.25\, d_p/\omega$.

2. The catalytically active material of claim 1, wherein the non-graphitizing carbon grains exhibit the following particle size distribution: d10=5 μm, d50=40 μm, and d90=150 μm.

3. The catalytically active material of claim 2, wherein the total mass fraction of nitrogen in the non-graphitizing carbon grains is less than 1 wt % of the total mass of the non-graphitizing carbon grains.

4. The catalytically active material of claim 2, wherein $d_p$ is in the range of 1 nm to 10 nm.

5. The catalytically active material of claim 2, wherein the material has been doped with a dopant metal selected from the group consisting of: Mn; Cu; and mixtures thereof, resulting in material that exhibits a molar ratio RDM=n (cobalt): n (dopant metal) in the range of 2 to 15.

6. The catalytically active material of claim 5, wherein Cu is used as a dopant resulting in material with a total mass fraction of Cu of less than $10^{-4}$ wt %.

7. The catalytically active material of claim 1, wherein the total mass fraction of nitrogen in the non-graphitizing carbon grains is less than 1 wt % of the total mass of the non-graphitizing carbon grains.

8. The catalytically active material of claim 7, wherein the material has been doped with a dopant metal selected from the group consisting of: Mn; Cu; and mixtures thereof, resulting in material that exhibits a molar ratio RDM=n (cobalt): n (dopant metal) in the range of 2 to 15.

9. The catalytically active material of claim 8, wherein $d_p$ is in the range of 1 nm to 10 nm.

10. The catalytically active material of claim 1, wherein $d_p$ is in the range of 1 nm to 10 nm.

11. The catalytically active material of claim 1, wherein $d_p$ is in the range of 2 nm to 6 nm.

12. The catalytically active material of claim 1, wherein the catalytically active material has been doped with a dopant metal selected from the group consisting of: Mn; Cu; and mixtures thereof, resulting in material that exhibits a molar ratio RDM=n (cobalt): n (dopant metal) in the range of 2 to 15.

13. The catalytically active material of claim 1, wherein the total mass fraction of Cu is less than $10^{-4}$ wt % of the total mass of the non-graphitizing carbon grains.

14. A process for making the catalytically active material of claim 1, comprising the following steps:
   (a) providing an aqueous solution comprising a metal precursor and an organic carbon source, wherein:
      the metal precursor comprises one or more organic, at least partially water soluble, salts of cobalt; and
      the organic carbon source comprises one or more saturated, aliphatic di-, tri-, or polycarboxylic acids;
   (b) spray drying or freeze drying the aqueous solution of the metal precursor and the organic carbon source, and thus obtaining intermediate product P; and
   (c) thermo-treating intermediate product P at a temperature in the range from 200° C. to 380° C.

15. The process of claim 14, wherein the organic carbon source is selected from the group consisting of: malonic acid; tartaric acid; citric acid; and mixtures thereof.

16. The process of claim 14, wherein intermediate product P is thermo-treated at a temperature in the range from 255° C. to 375° C. for 1 to 4 hours.

17. The process of claim 14, wherein an intermediate product P is thermo-treated at a temperature in the range from 300° C. to 350° C. for 1 to 4 hours.

18. A chemical reaction comprising the catalytically active material of claim 1, as a catalyst.

19. The chemical reaction of claim 18, wherein the reaction is a hydrogenation of organic compounds; a reductive amination of carbonyl compounds; or a hydroformylation of organic compounds.

20. The chemical reaction of 18, comprising reacting carbon monoxide, carbon dioxide or mixtures thereof, with hydrogen, to form alcohols, alkenes, alkanes or mixtures thereof.

\* \* \* \* \*